(12) United States Patent
Dominick et al.

(10) Patent No.: US 9,597,039 B2
(45) Date of Patent: Mar. 21, 2017

(54) DEVICES, METHODS AND COMPUTER READABLE MEDIUMS FOR ON DEMAND PERSONALIZATION OF A USER INTERFACE

(71) Applicant: Siemens Aktiengesellschaft, Munich (DE)

(72) Inventors: Lutz Dominick, Eggolsheim (DE); Vladyslav Ukis, Nuremberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 542 days.

(21) Appl. No.: 13/803,694

(22) Filed: Mar. 14, 2013

(65) Prior Publication Data

US 2014/0281959 A1   Sep. 18, 2014

(51) Int. Cl.
*A61B 5/00* (2006.01)
*G06F 19/00* (2011.01)

(52) U.S. Cl.
CPC .......... *A61B 5/7425* (2013.01); *G06F 19/322* (2013.01)

(58) Field of Classification Search
CPC ............. G06F 9/45512; G06F 11/3414; G06F 9/4443; G06F 9/4446; G06F 3/0481; G06F 19/3487; G06F 19/3443; G06F 17/243; G06F 19/321; G06F 19/32; G06F 2203/04803; G06Q 50/24
See application file for complete search history.

(56) References Cited

U.S. PATENT DOCUMENTS

| | | | | |
|---|---|---|---|---|
| 2003/0107596 A1* | 6/2003 | Jameson | ............... | G06F 9/4443 715/762 |
| 2008/0133287 A1* | 6/2008 | Slattery | ............... | G06F 11/3419 705/32 |
| 2009/0187407 A1* | 7/2009 | Soble | .................. | G06F 19/3487 704/260 |
| 2009/0265719 A1* | 10/2009 | Meijer | ............... | G06F 9/45512 719/320 |
| 2011/0225493 A1* | 9/2011 | Uchida | ............. | G06F 17/30011 715/704 |
| 2012/0054230 A1* | 3/2012 | Kanada | .......................... | 707/769 |
| 2012/0123975 A1* | 5/2012 | Lin | ........................ | G06F 9/4446 706/11 |
| 2013/0055095 A1* | 2/2013 | Kavanagh | ..................... | 715/738 |
| 2013/0111372 A1* | 5/2013 | Herlitz | ........................... | 715/762 |
| 2013/0151286 A1* | 6/2013 | Kablotsky et al. | ............... | 705/3 |
| 2013/0339051 A1* | 12/2013 | Dobrean | ............. | G06F 19/3487 705/3 |
| 2014/0123061 A1* | 5/2014 | Bennett et al. | ............... | 715/808 |

\* cited by examiner

*Primary Examiner* — Jeffrey A Gaffin
*Assistant Examiner* — Mandrita Brahmachari
(74) *Attorney, Agent, or Firm* — Harness, Dickey & Pierce, P.L.C.

(57) ABSTRACT

A clinical workstation includes a processing unit configured to record context information and user habit information based on user interaction with a computer-based application during a plurality of phases of a medical workflow. The processing unit may also be configured to generate a plurality of macro sets based on the recorded context information and the recorded user habit information. Each macro set may be associated with at least one user preferred application tool and be bound to one of the plurality of phases.

27 Claims, 8 Drawing Sheets

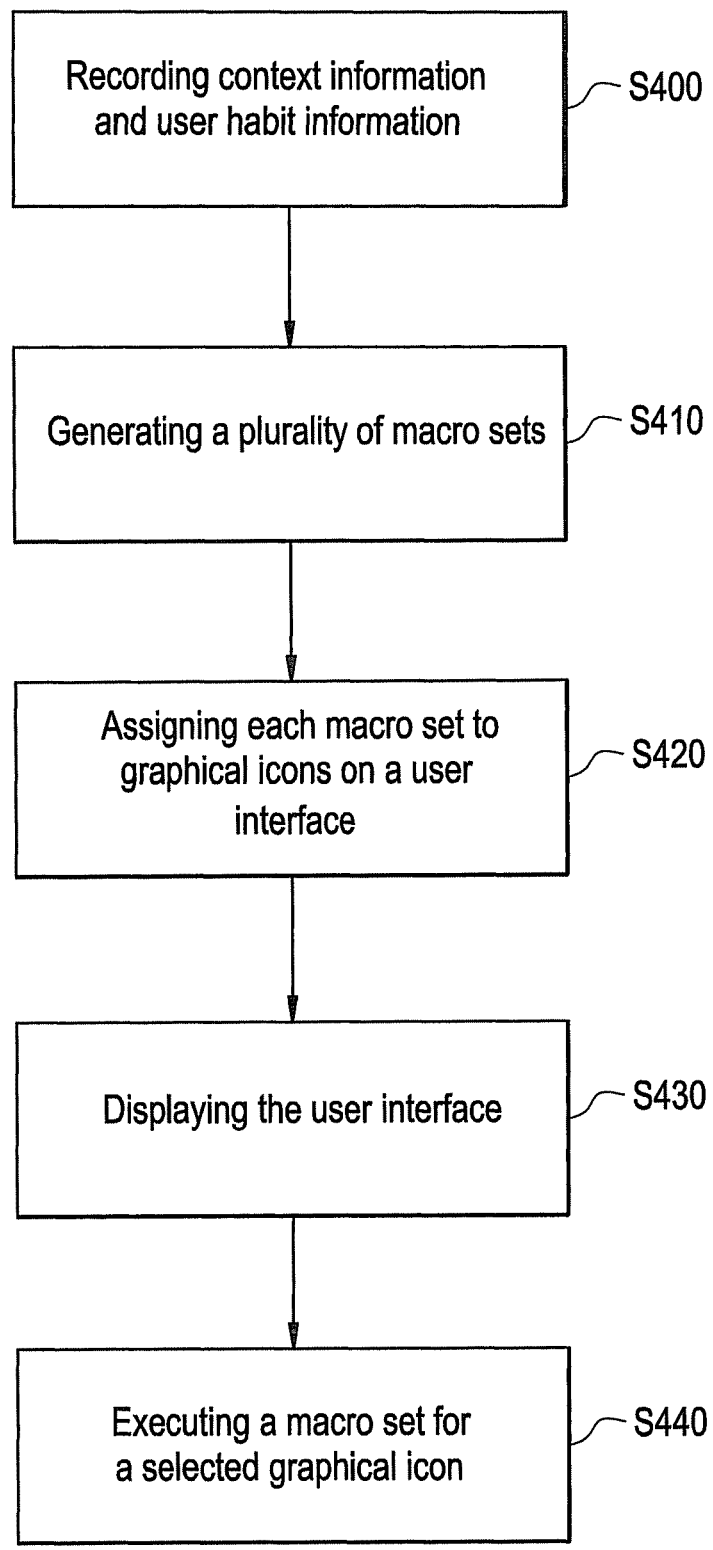

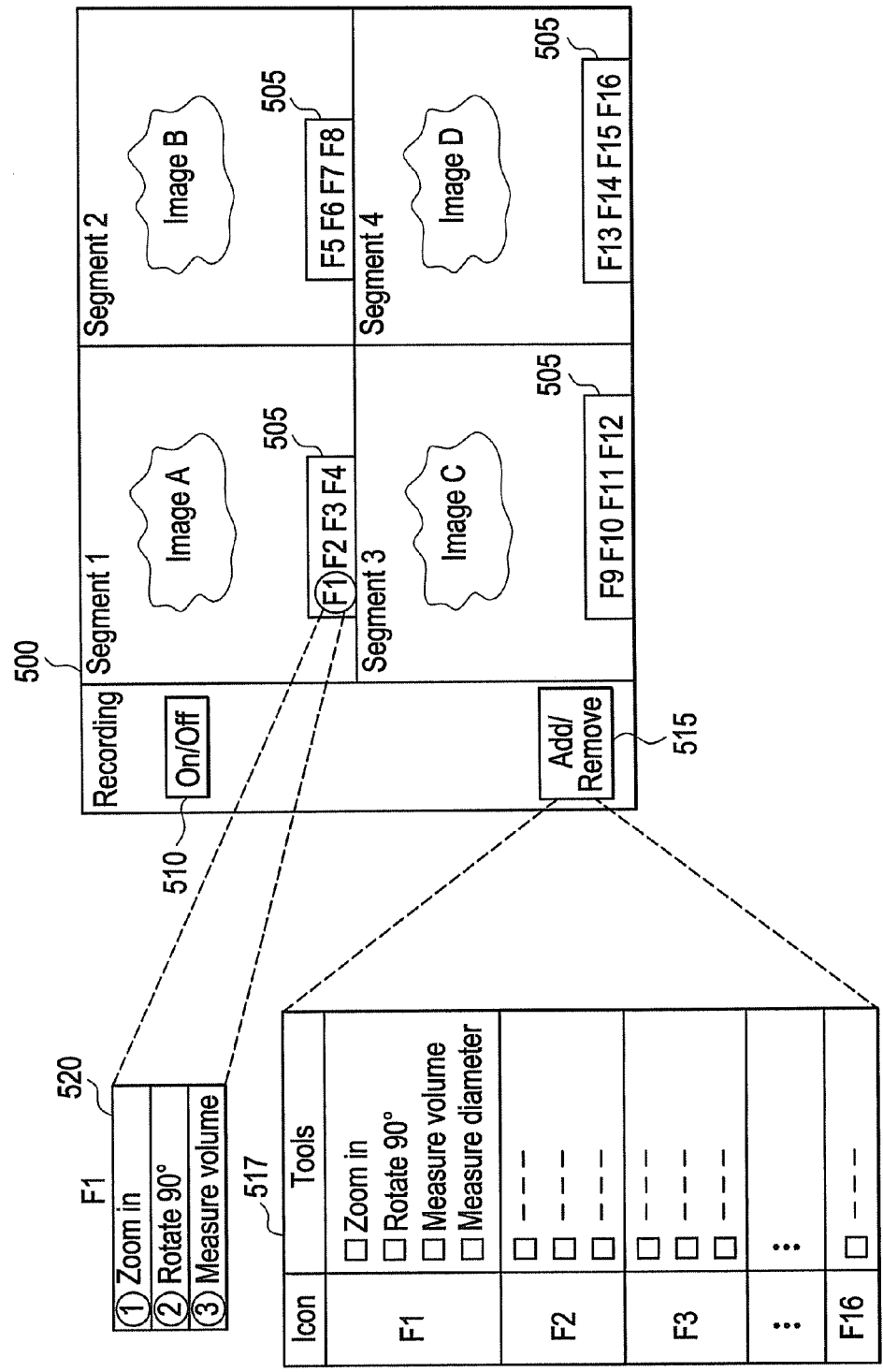

DEVICES, METHODS AND COMPUTER READABLE MEDIUMS FOR ON DEMAND PERSONALIZATION OF A USER INTERFACE

BACKGROUND

Medical diagnoses are often made after an examination of relevant images or other data on a clinical workstation (e.g., a personal computer, laptop, tablet, etc.). Such an examination is usually performed with the assistance of a computer based imaging application after images are obtained through an imaging scan (e.g., a PET scan, a MRI scan, etc.). For example, if a user of the clinical workstation (e.g., a physician, radiologist, etc.) would like to evaluate and diagnose a heart of a particular patient, the user opens the computer based application on a user interface (using, for example, a monitor other display), selects the patient's file to display images of the patient's heart obtained by the imaging scan, evaluates the images with the assistance of one or more application tools, and makes a diagnosis based on the evaluation. The time spent examining each case becomes an issue as the pressure on clinicians to examine more cases increases.

Conventional computer based applications attempt to address this issue with display protocols (DiPs) on a per-application basis. For example, DiPs allow clinicians to ensure that their medical workspace (i.e., the hanging protocol) looks the same way when they open a next case. In other words, conventional applications display a user interface (UI) layout before the user has seen the images undergoing diagnosis. Thus, the available diagnostic functionality of the application has to be decided by the user prior to the start of the application (e.g. in workflow mapping or ad-hoc task selection) without the user having seen the images, even though the proper choice of such functionality is important to diagnosis. The problem is that the applications, task flows, and preprocessing are not personalized, and no preserved user knowledge is available when a similar context re-appears. In other words, clinicians waste time selecting the proper diagnostic functionality of the application for each new case even if the new case requires similar diagnostic functionality as a previous case. Accordingly, clinicians wish to customize and personalize the applications to increase efficiency and performance.

SUMMARY

At least one example embodiment relates to methods, devices, and/or computer program products for personalization of a user interface.

According to at least one example embodiment, a clinical workstation includes a processing unit configured to record context information and user habit information based on user interaction with a computer-based application during a plurality of phases of a medical workflow. The processing unit may also be configured to generate a plurality of macro sets based on the recorded context information and the recorded user habit information. Each macro set may be associated with at least one user preferred application tool and being bound to one of the plurality of phases.

According to at least one example embodiment, the clinical workstation further includes a display configured to display a user interface of the computer-based application. The processing unit may be further configured to assign each macro set to graphical icons of the user interface, the graphical icons automating a usage of the at least one user preferred application tool.

According to at least one example embodiment, the processing unit is configured to record the context information and the user habit information in response to a user initiated event.

According to at least one example embodiment, the processing unit is configured to store the plurality of macro sets in an external database.

According to at least one example embodiment, upon selection of one of the graphical icons, the processing unit is configured execute the macro set assigned to the selected graphical icon such that the at least one preferred application tool is executed on the user interface.

According to at least one example embodiment, the processing unit is further configured to query the external database to recall a stored macro set and assign the recalled macro set to the one or more graphical icons to generate updated graphical icons. The processing unit may be configured to display the updated graphical icons on the interface.

According to at least one example embodiment, the processing unit is configured to query the external database in response to a user request.

According to at least one example embodiment, the processing unit is configured to automatically query the external database.

According to at least one example embodiment, the processing unit is configured to execute the recalled macro set associated with the updated graphical icons such that functions of the user preferred application tools are executed on the interface.

According to at least one example embodiment, the processing unit is configured to allow the user to assign the recalled macro set to the graphical icons.

According to at least one example embodiment, the processing unit is configured to automatically assign the recalled macro set to the graphical icons based on previously recorded context information and user habit information stored in the database.

According to at least one example embodiment, a method includes recording context information and user habit information based on user interaction with a computer-based application during a plurality of phases of a medical workflow. The method may also include generating a plurality of macro sets based on the recorded context information and the recorded user habit information. Each macro set may be associated with at least one user preferred application tool and be bound to one of the plurality of phases.

According to at least one example embodiment, the method further includes assigning each macro set to graphical icons on a user interface of the computer-based application, the graphical icons automating a usage of the at least one user preferred application tool and displaying the user interface on a display.

According to at least one example embodiment, the recording the context information and the user habit information occurs in response to a user initiated event.

According to at least one example embodiment, the method further includes storing the plurality of macro sets in an external database.

According to at least one example embodiment, further includes executing, upon selection of one of the graphical icons, the macro set assigned to the selected graphical icon such that the at least one preferred application tool is executed on the interface.

According to at least one example embodiment, the method further includes querying the external database to recall a stored macro set and assigning the recalled macro set to the one or more graphical icons to generate updated graphical icons. The method may also include displaying the updated graphical icons on the user interface.

According to at least one example embodiment, the querying the external database occurs in response to a user request.

According to at least one example embodiment, the querying occurs automatically.

According to at least one example embodiment, the method further includes executing the recalled macro set associated with the updated graphical icons such that functions of the user preferred application tools are executed on the interface.

According to at least one example embodiment, the method further includes allowing the user to assign the recalled macro set to the graphical icons.

According to at least one example embodiment, the method further includes automatically assigning the recalled macro set to the graphical icons based on previously recorded context information and user habit information stored in the database.

According to at least one example embodiment, the method further includes dividing the medical workflow into the plurality of phases.

According to at least one example embodiment, a non-transitory computer readable medium includes instructions for, if executed by a computer processor, causing the computer processor to implement the above described method.

According to at least one example embodiment, an interface for a computer-based application includes at least one segment configured to display an image related to a medical workflow and at least one first icon configured to automate a usage of at least one user preferred application tool of the computer-based application. The at least one first icon may be assigned to the at least one segment and associated with one or more macros. The one or more macros may be based on context information and user habit information recorded during user interaction with the at least one segment.

According to at least one example embodiment, the user interface may further include a second icon configured to control whether a processor records the user context information and user habit information and a third icon configured to allow the user to at least one of add and remove user preferred application tools to or from the at least one icon.

BRIEF DESCRIPTION OF THE DRAWINGS

In the detailed description of example embodiments given herein below and the accompanying drawings, like elements are represented by like reference numerals, which are given by way of illustration only and thus are not limiting of example embodiments and wherein:

FIGS. 4A and 4B illustrate example operations of the client workstation from FIG. 2 according to at least one embodiment;

FIG. 5 illustrates an example layout of a user interface for the display of the client workstation shown in FIG. 2 according to at least one embodiment.

Figure 1:
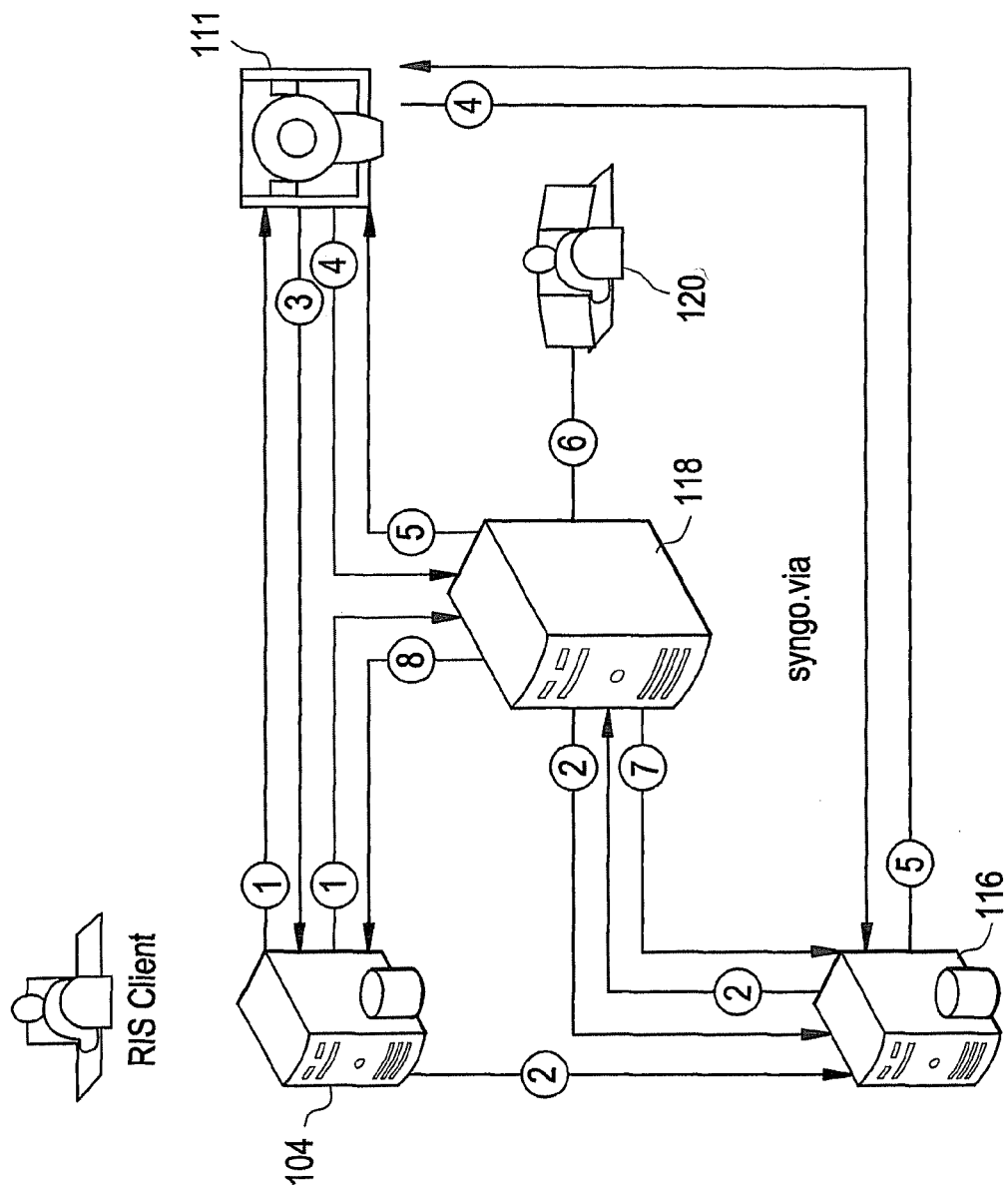
FIG. 1 illustrates a high level system architecture in which example embodiments may be implemented.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF EXAMPLE EMBODIMENTS

While example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium. A processor(s) will perform the necessary tasks.

Specific structural and functional details disclosed herein are merely representative for purposes of describing example embodiments of the present invention. Example embodiments may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art.

In the following description, illustrative embodiments will be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

In some environments (e.g., syngo.via), individual software application elements are processed by a user in a defined sequence. The individual software-application building blocks (e.g., tasks) and sequence of tasks are configured. A sequence of tasks is referred to as a task flow or a workflow. Task flows (or workflows) define both a position of the tasks and the data links between the tasks. The data links ensure that the output data of one task function is used as input data for a subsequent task. Tasks can typically be executed sequentially, in parallel, or in an arbitrary sequence.

Example embodiments provide methods, apparatuses and computer readable storage mediums for automatically capturing and assembling macros for efficient and reliable automation of user interaction across workflows and/or across independent applications. Assembled macros may be stored in, for example, an associated repository or database and used in subsequent workflows.

FIG. 1 illustrates a syngo architecture in which example embodiments may be implemented. The syngo architecture will be described with regard to the signal flow diagram shown in FIG. 1. Because the components of the syngo architecture themselves are generally well-known, a detailed discussion of each component is omitted.

Referring to FIG. 1, at (1) a radiology information system (RIS) server 104 schedules a patient by sending a work list to the modality 111. In one example, the RIS server 104 schedules a CT scan on a CT Modality by sending the work list to the CT modality. The RIS server 104 also sends the work list to the syngo.via server 118 to inform the syngo.via server 118 about that scan work item, which may contain multiple scan series over a couple of visits.

At (2), the RIS server 104 and/or the syngo.via server 118 pre-fetch prior studies for a patient from a picture archiving and communication system (PACS) server 116. The prior studies may include prior findings that the syngo.via server 118 may compare against the current scan and the findings in the prior scan.

At (3), the RIS server 104 receives procedure information (e.g., treatment details for accounting) back from the modality 111.

At (4), the modality 111 sends images to the syngo.via server 118 for creation of findings, comparison to prior findings, and to the PACS server 116 for archiving.

At (5), the syngo.via server 118 informs the modality 111 that all data for the patient has been archived. In response, the modality 111 is able to delete that data on the modality 111.

At (6) a clinical user 120 performs a reading activity and creates the findings on the scanned images. The clinical user 120 then summarizes the findings in a clinical report.

At (7), the clinical report is stored at the PACS server 116. Structured reporting of the report is also stored in the PACS server 116 (e.g., for archiving).

At (8), the syngo.via server 118 informs the RIS server 104 that the report has been signed-off (e.g., for accounting).

The findings are created and reported, and may also be re-animated, on the syngo.via server side. The findings are archived in a clinical report at the PACS server 116. So the reading applications on the syngo.via server 118 show findings that are either newly created, or those that were created in prior studies some time ago.

Figure 2:
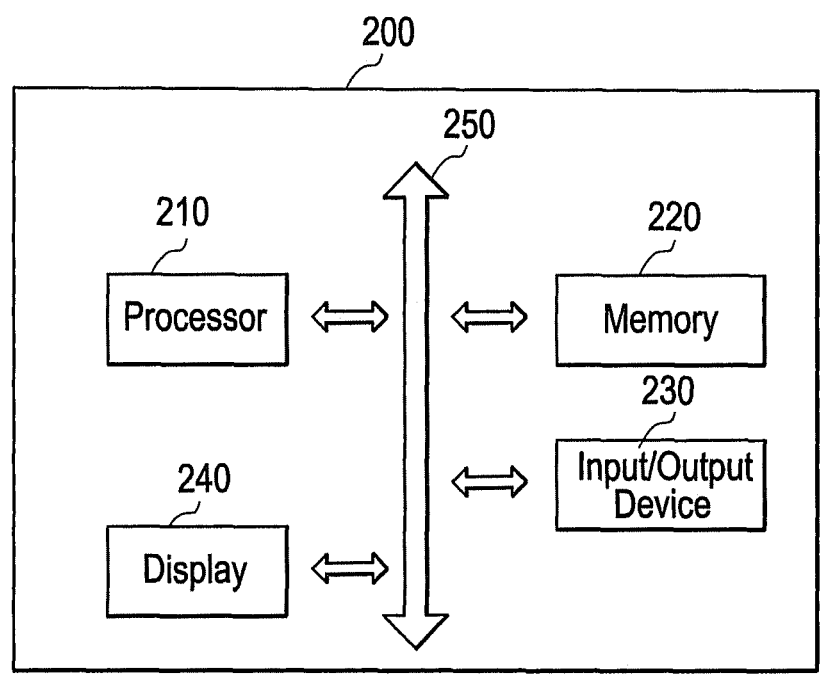
FIG. 2 illustrates a client workstation according to at least one example embodiment.

FIG. 2 illustrates a client workstation according to an example embodiment. The client workstation 200 includes a processor 210, an input/output device 230, a memory 220, a display 240, a bus 250. The client workstation 200 may be, for example, a personal computer configured for use by the clinical user 120 in FIG. 1 to examine medical data.

The processor 210, input/output device 230, memory 220 and display 240 may perform data communication with each other by using a bus 250. The processor 210 may execute a program by accessing the memory 220 through the bus 250. The input/output device 230 may be used to input/output data to/from the client 200. The client workstation 200 may connect to external devices (e.g. the servers from FIG. 1) by using the input/output device 230 and may exchange data with the external devices. The display 240 may display a user interface based on commands received from a user of the client workstation 200 and/or commands received from the processor 210.

The memory 220 may store codes or programs for operations of the processor 210. For example, the memory 220 may include a data structure including instructions to execute the method described below in reference to FIGS. 5A and 5B. The memory 220 may store a user-interface container configured to host a patient browser and a plurality of imaging applications. Each of the applications may be independent and may be associated with the syngo architecture described in FIGS. 1 and 3. The applications may be medical imaging applications which are designed according to the images created by the system of FIG. 1. Examples include a Coronary image analysis application, a Colon image analysis application, and a cardio vascular application.

For the purposes of clarity, "different imaging application" may refer to a different version of an application, a different application and different versions of different imaging applications being based on different versions of the same product-line code.

The memory 220 may include one or more memory modules. The memory modules may be separate physical memories (e.g., hard drives), separate partitions on a single physical memory and/or separate storage locations on a single partition of a single physical memory. The memory modules may store information associated with the installation of software (e.g., imaging processes).

It should be understood that a processor 210, such as a digital signal processor or a microcontroller, is specifically programmed to execute the instructions stored in the memory 220. For example, the processor 210 is specifically programmed to execute instructions stored in the memory 220 according to the example operations of FIGS. 5A and 5B, which are described in greater detail below.

Figure 3:
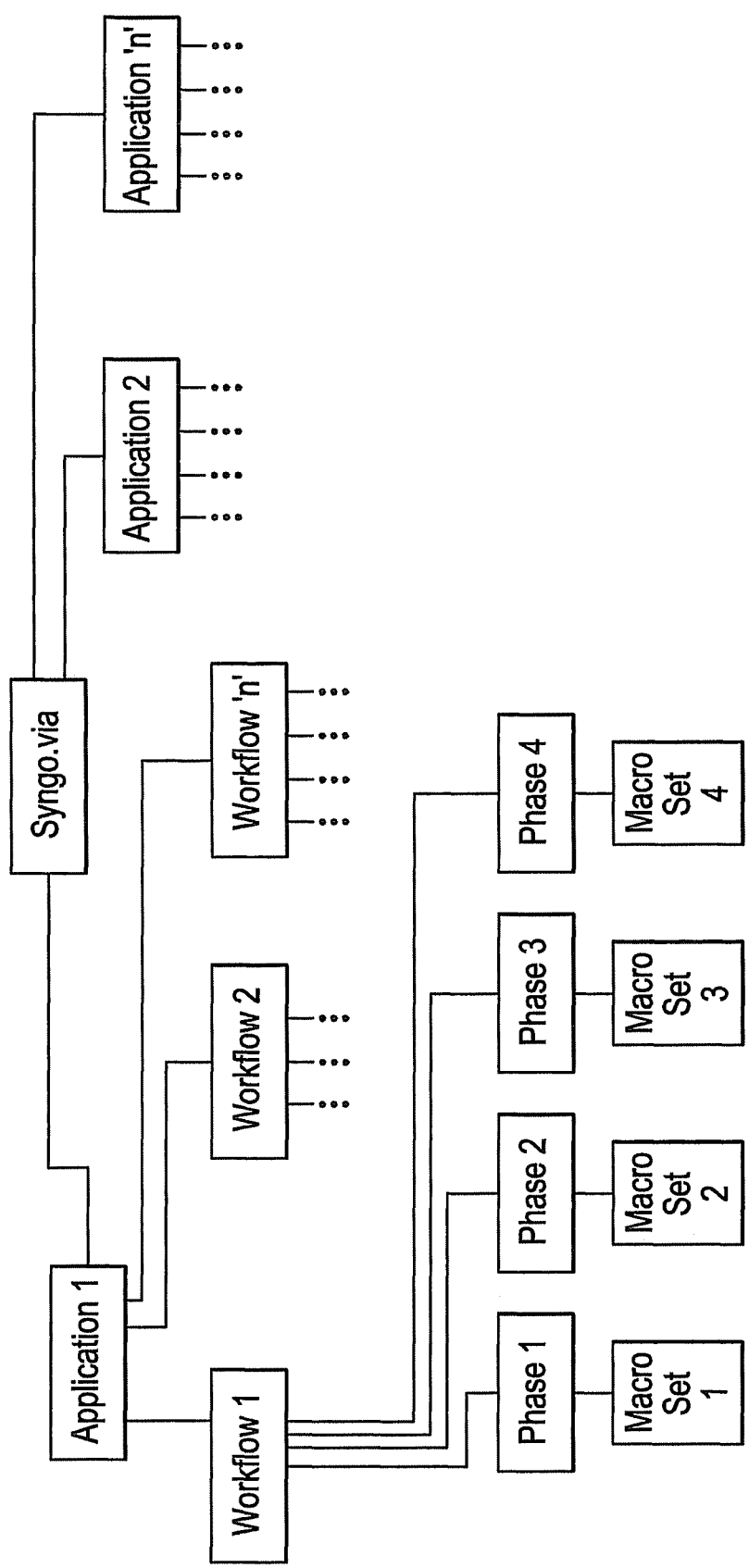
FIG. 3 illustrates an example hierarchy diagram of the system architecture from FIG. 1 according to at least one embodiment.

FIG. 3 illustrates an example hierarchy diagram of the syngo.via architecture from FIG. 1 according to at least one embodiment.

FIG. 3 illustrates that syngo.via may have a number of computer-based imaging applications 1, 2 . . . n. Each application may include multiple workflows 1, 2 . . . n. Each of the applications may be independent and may be associated with the syngo architecture as described in FIG. 1. In one embodiment, a workflow is divided into dedicated phases according to existing structures of the medical domain, the clinical workflow steps, and/or user interface (UI) layouts (e.g. as defined in the extensible application markup language (XAML) files of the applications). Accordingly, each phase may correspond to only part of the overall workflow. Thus, it should be understood that a particular workflow or task flow may include a plurality of phases.

For example, if the workflow is divided into phases according to existing structure of the medial domain, phase 1 of application 1 may be a phase for "workflow selection" which includes steps associated with selecting a particular workflow for application 1. Phase 2 of application 1 may be a phase for "preprocessing" which includes steps associated with booting up application 1 (e.g., volume creation). Phase 3 may be a phase for "user interaction" which may include the steps associated with a user interacting with the interface for application 1. Although particular phases have been shown and described, it should be understood that the scope of these phases is not limited thereto. For example, each phase could correspond to a particular segment of a user interface, as described in more detail below in FIG. 5. Further, each phase may have any number of sub-phases.

Referring to FIGS. 2 and 3, the processor 210 generates and maps a macro set (i.e., an individual macro or multiple macros) to each phase by recording, evaluating, and filtering the ongoing activity (e.g., user activity) in each phase. Each macro set may be a program or set of programs with pluggable handlers that are assigned to, for example, a graphical icon on a user interface at run-time. As such, each macro may be a collection of extensible markup language (XML) elements that point to an application handler's dynamic link library (DLL) which may contain the tool names (e.g., rotate 90°, zoom, etc.) from the application's configuration files. The application's configuration files may contain sub-handler DLLs and other XML configurations of the application's features.

The processor 210 may record user activity in accordance with any well-known method of tracking user interaction on an interface. However, unlike the conventional art, the processor 210 is capable of keeping track of both the user interaction as well as the phase (i.e., where in the overall workflow the user interaction is taking place) in which the user interaction is recorded. This is possible because the workflow/taskflow and applications are configured using some dialect of an extensible markup language (XML), e.g. extensible application markup language (XAML) for the application UI configuration. The processor 210 reads, adapts and interprets these XML configurations for its purposes, while, for example, the application XAML configuration is interpreted by the application as the UI configuration at the same time.

Within the present description, XAML may be understood as an XML dialect used to configure at least the layout of a user interface and connect application tool handlers to the user interface elements (e.g. clickable icons). In general, XML and/or XAML define tree-like element structures, and according to one embodiment of this application, dedicated areas of a user interface are based on sub-trees in the tree-like structure. XML and XAML trees and sub-trees are generally well known in the art as being used to configure application user interfaces. As such, a detailed description of the XML and XAML concepts is omitted from this description. An example of how the processor 210 records, evaluates, and filters the information for each phase is described below.

In at least one example embodiment, the processor 210 evaluates the XAML elements of the imaging application, not for building the UI, but for detecting the boundaries of the phases from the XAML. According to at least one example embodiment, the processor 210 identifies a sub-tree in an XAML file as a phase on which to use an additional proprietary extensible markup language (XML) attribute (e.g., 'phase=ON') as a first XML element of a sub-tree. Optionally, the processor 210 marks subparts of that XML tree with the attribute 'phase=OFF' for selected XML elements where such subtrees begin.

As an alternative to explicitly marking phases as described above, the processor 210 may read the well-known controls within the application, like "Panel", "Canvas", or other areas (e.g., rectangles) that structure the UI as boundaries for phases. Such controls are at the beginning of a subtree with more controls underneath.

Other additional attributes that are not evaluated by the UI building process or further hidden attributes may also be set by the processor 210. For example, the processor 210 may set 'phasename=<name>' upon detecting that a set of steps has been repeated during user interaction.

The processor 210 performs at least the following operations to prepare macro recording. First, the processor 210 builds a tree of phases with identifiers/names for each phase. Second, from the XAML elements of the imaging application, the processor 210 detects UI Controls which register handlers (these handlers call the tools and are invoked by e.g., user mouse clicks on menus). For each phase, the processor 210 collects these UI controls (e.g., UI control names, often already the tool names, and the XAML element path to control names) and UI control handlers (during replay of a macro, these UI control handlers are called).

Moving forward, for each phase and UI control, the processor 210 registers a processor 210-generic-handler (in the same way as the UI control does) with the parameters Phase-Identifies and UI-Control-Identifier and UI-Control-Path. This ensures that the processor 210 recognizes when the user is interacting with the UI by, for example, clicking on a menu icon. Finally, the processor 210 uses the above identifiers and the processor's own generic handler to match the UI control handler invocation to the correct location in the phase tree.

The identifiers described above may be, for example, global unique identifiers (GUIDs) generated by the processor 210. This ensures unambiguous identification of all UI elements in hash maps.

One option to register an additional handler is to place a XAML expression next to the UI-Control's handler. Another option is to generate a separate XAML element that contains the UI Control's handler and the processor's handler in a way that the XAML mechanism registers additional handlers.

During run-time, the processor 210 detects the phase and records user interaction with the UI (i.e., records UI Control handlers associated with the user interaction) even if the user has switched to another phase or is still in the same phase. As such, macro recording and replay is phase specific.

Also, the user can be offered to delete recorded macro steps from a phase specific macro recording before saving a macro and binding it to a replay icon on the UI. Further, the user may be allowed to combine macros from a set of macros for a particular phase. Because the UI Controls and handlers are only 'declared' in XAML elements (in contrast to source code statements), and because XAML files are re-used across multiple imaging applications, the macro sets in one imaging application may match the XAML files in other, different imaging applications.

As shown in FIG. 3, macro set 1 is mapped to phase 1, macro set 2 is mapped to phase 2, and so on. Importantly, each individual macro or macro set is bound or restricted to a particular phase. For example, macro set 2 is bound or restricted to phase 2 and cannot be used in phases 1 or 3. This reduces (or alternatively, eliminates) the risk of malfunction during macro replay.

It should be understood that the macros may be compatible with multiple software architectures. Thus, the macros do not have to be changed in order to execute the macros on a different imaging application. According to an example embodiment, if the tools and features of the sub-handler design in, for example, syngo.via are used as the standard, the macros may be compiled into sub-handlers for syngo.via applications. However, macros may be compiled in multiple ways. For example, in another embodiment, if the imaging application is based on Eclipse, the XML elements in syngo.via may be compiled into Eclipse compliant macros with, for example, a cross-compiler. Here, it is important for the processor to map control names of the icons in the syngo.via application and the control names in Eclipse XML onto each other. Cross-compilers are well known within the art, and as such, a detailed description of how macros may be compatible with multiple software architectures using a cross-compiler is omitted from this description.

Figure 4B:
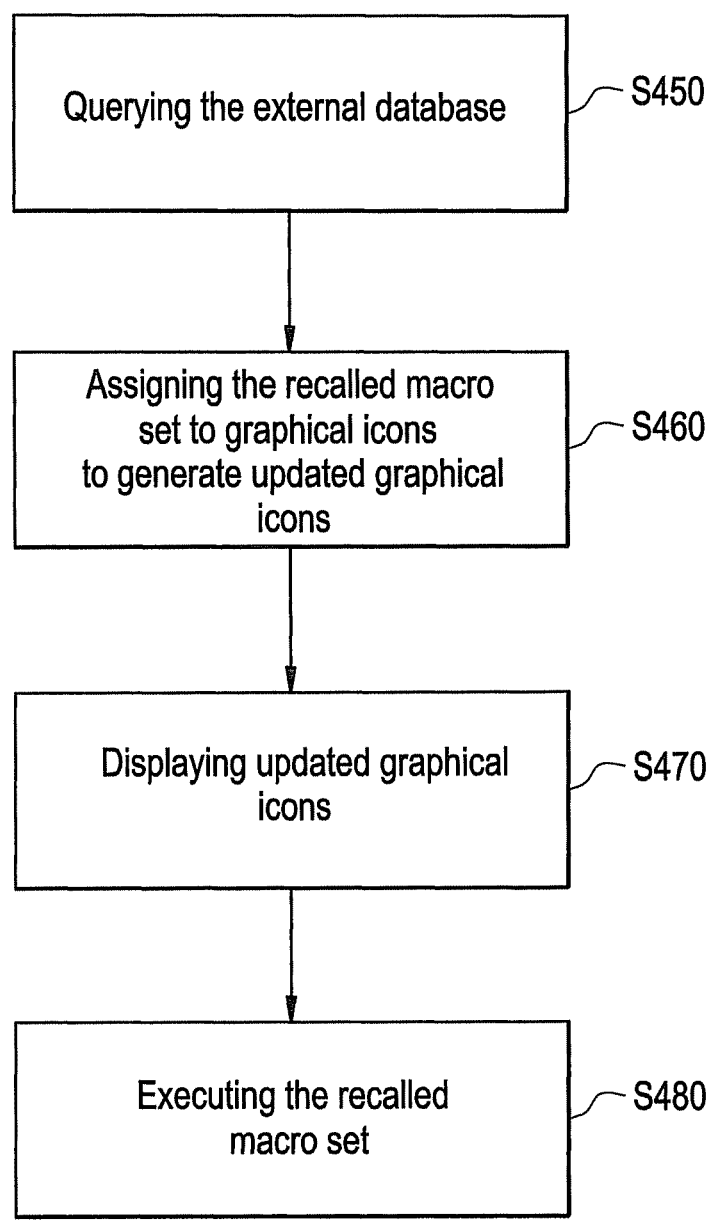

FIGS. 4A and 4B illustrate example operations of the client workstation from FIG. 2 according to at least one embodiment.

For example, the steps shown in FIGS. 4A and 4B may be carried out by processor 210 from FIG. 2 for one of the computer based imaging applications of FIG. 3. Accordingly, FIGS. 4A and 4B are described below with reference to FIGS. 2 and 3.

As shown in step S400, a method according to at least one example embodiment includes recording context information and user habit information based on user interaction with a computer-based imaging application. For example, the processor 210 may be configured to record context information and user habit information based on user interaction with one of the computer-based imaging applications shown in FIG. 3. The processor may record this information according the process described above with reference to FIG. 2. Step S400 may occur in response to a user initiated event. For example, the process may be configured to begin recording context and user habit information upon a user's selection of a "record" function (e.g., a "Record" icon on a user interface).

According to at least one example embodiment, context information includes application names (or other identifiers provided by the application's XAML, like the XAML file name), phase names (or other identifiers, like the path to the phase in the XAML file), and/or image data types (like CT, MR, MI, which is optional information). With respect to image data types, a plug-in may be provided so that the processor 210 can read the data type from an interface provided by the application).

According to at least one example embodiment, user habit information includes the sequence of UI interaction steps that the user has performed and/or a user-defined subset of steps (in case the user deleted steps), which the user has finally saved in macro sets. However, example embodiments are not limited thereto. User habit information may include any desired user interaction with the user interface.

According to at least one example embodiment, the processor 210 records the context information and user habit information during each of a plurality of phases of a medical workflow. For example, with reference to FIG. 3, the processor 210 matches user interface (UI) interactions of the user with the XAML UI definition to determine that the user is in phase 1, and then records events and user interaction with UI icons for as long as the user is in phase 1. For example, the processor 210 records a user's click on a corner menu item.

As shown in step S410, the method further includes generating a plurality of macro sets based on the recorded context information and the recorded user habit information. For example, the processor 210 may generate the plurality of macro sets based on the recorded context information and the recorded user habit information. Here, the processor 210 may also ensure that each macro set is bound to one of the plurality of phases (i.e. although macro sets may be identical, a particular macro set cannot be used for more than one phase).

In step S410, each macro set is associated with at least one user preferred application tool. User preferred application tools for a particular phase may be defined as tools that are commonly used in that phase. For example, the tools 'zoom in', 'rotate 90°', and 'measure volume' may be frequently selected by a user in phase 1. Thus, the tools 'zoom in', 'rotate 90°,' and 'measure volume' may be considered as user preferred application tools for phase 1. The processor 210 may be configured to associate each macro set with one or more preferred application tools.

As shown in step S420, the method may include assigning each macro set to graphical icons on a user interface. Further, as shown in step S430, the method may include displaying the user interface on a display. For example, the processor 210 may be configured to assign each macro set to graphical icons on a user interface of the computer-based application and then display the user interface on a display (e.g., display 240).

It should be understood that assigning a macro set to an icon may include removing functionality from the macro set and/or adding additional functionality to the macro set. For example, the user may be allowed to add and/or remove application tools to the recalled macro set via a checkbox or other appropriate user interface element. In this case, the processor 210 may be configured to generate the checkbox and/or populate the checkbox with options for additional tools based on previously recorded context information and user habit information.

Alternatively, the processor 210 may automatically (i.e., without user selection) add and/or remove tools to/from the macro set based on previously recorded context information and user habit information.

Although not shown in FIG. 4A, the method may also include storing the plurality of macro sets in an external database. For example, the processor 210 may store the plurality of macro sets in an external database (e.g., database 450 in FIGS. 4A-4C) after or in conjunction with performing step S410. As such, it may be said that macros are auto-collected and offered to the user for later use.

As shown in step S440, the method may further include executing, upon selection of one of the graphical icons by a user, the macro set assigned to the selected graphical icon such that the at least one preferred application tool is executed on the user interface. For example, processor 210 may be configured to execute the macro set assigned to the selected graphical icon such that the at least one preferred application tool is executed on the user interface. A more detailed explanation of the graphical icons and the user interface are discussed below with reference to FIG. 6.

Although not shown in FIG. 4A, it should be understood that the method may include dividing the medical workflow into the plurality of phases. This step may occur before step S400. For example, the processor 210 may be configured to divide the medical workflow into the plurality of phases based on a user's instructions. Alternatively, the processor 210 may automatically divide the medical workflow into the plurality of phases based on context information and user habit information recorded during a previous workflow. For example, the processor 210 may associate a set of workflow steps with a first phase, and upon detecting the same set of steps in a subsequent workflow, the processor 210 may automatically detect that the workflow is in the first phase.

FIG. 4B illustrates an example operation of a processor according to an example embodiment. It should be understood that the method of FIG. 4B may be carried out in conjunction with or separate from FIG. 4A.

As shown in step S450, the method may include querying an external database to recall a stored macro set. For example, the processor 210 may query an external database (e.g., database 650 from FIG. 6) to recall a stored macro set. In one example embodiment, the processor 210 may query the database in response to a user initiated event (e.g., a user request, in response to clicking on an interface icon). Alternatively, the processor may query the database automatically (e.g., when the user initially opens the imaging application, changes to a different imaging application, and/or enters a new phase).

As shown in step S460, the method may include assigning the recalled macro set to the one or more graphical icons to generate updated graphical icons. For example, the processor 210 may assign the recalled macro set to update the one or more graphical icons. Accordingly, the updated graphical icons are associated with the user-preferred tools of the recalled macro set.

It should be understood that step S460 may include removing functionality from the recalled macro set and/or adding additional functionality to the recalled macro set to the graphical icons. For example, the user may be allowed to add and/or remove application tools to the recalled macro set via a checkbox or other appropriate user interface element. In this case, the processor 210 may be configured to generate the checkbox and/or populate the checkbox with options for additional tools based on previously recorded context information and user habit information. Alternatively, the processor may automatically (i.e., without user selection) add and/or remove tools to/from the recalled macro set based on previously recorded context information and user habit information stored in a database (e.g., database 650 form FIG. 6).

As shown in step S470, the method may further include displaying the updated graphical icons. For example, the processor 210 may display the updated graphical icons on the user interface.

As shown in step S480, the method may include executing the recalled macro set upon selection of one of the updated graphical icons. For example, the processor 210 may be configured to, upon selection of one of the updated graphical icons, execute the recalled macro set associated with the updated graphical icons such that functions of the user preferred application tools associated with the recalled macro set are executed on the user interface.

FIG. 5 illustrates an example layout of a user interface for the display of the client workstation shown in FIG. 2. Accordingly, FIG. 5 is described below with reference to FIG. 2.

FIG. 5 illustrates an example layout of a user interface (UI) 500 on the display 240 of client workstation 200 in FIG. 2. In FIG. 5, the UI 500 is divided into segments 1, 2, 3, and 4. Each segment has an associated image A, B, C, and D. Images A, B, C, and D may be, for example, different views of the same object undergoing examination (e.g., image A may be a cross section of a heart, image B may be a 3-D rendering of the same heart, etc.).

For convenience of explanation, in FIG. 5, each of segments 1, 2, 3, and 4 may be correspond to phases 1, 2, 3, and 4, respectively, from FIG. 3. In other words, for phase 1, the processor 210 records user interaction within segment 1; for phase 2, the processor 210 records user interaction with segment 2; for phase 3, the processor 210 records user interaction with segment 3; and for phase 4, the processor 210 records user interaction with segment 4. Images A, B, C, and D may be obtained via a medical imaging scan (e.g., a MRI, a PET scan, a CT scan, etc.). According to at least one example embodiment, the UI 500 includes a recording icon 510, which allows for the user to switch the recording function of the processor 210 on and off, as desired.

While recording user interaction (i.e., context information and user habit information) within each phase, the user actions are filtered such that only the 'systematic' actions are used to generate a macros. For example, with reference to FIG. 5 and an examination of heart images A, B, C, D for 'patient X,' the processor 210 is configured to record a user's sequence of tool selection (e.g., a user's sequential selection of 'zoom in, rotate 90°, measure volume') in segment 1. However, the processor 210 does not capture, for example, arbitrary scrolling in segment 1 because scrolling is not as useful for future automation.

These filtered 'systematic' actions may be stored in a cloud based repository or database (e.g., database 650 in FIGS. 6A-6C, which may be a database at syngo.via server 118 from FIG. 1) as macros. Because the content of this database is software programs (i.e. macros), and not medical data, legal restrictions that can hamper the export of data from the hospital to a public cloud environment do not apply. If the user later begins a heart examination for a different patient, e.g., 'patient Y,' the processor may recognize that the user is examining patient Y's heart in a familiar phase (e.g., segment 1), recall the macro(s) stored for segment 1 of patient X, and assign the recalled macro(s) to an icon(s) in segment 1.

Referring to FIG. 5, UI 500 includes graphical icons 505 (e.g., F1-F16). Graphical icons 505 are displayed in segments 1, 2, 3, 4, (as desired by a user or automatically). The processor 210 has assigned a macro set to each of these graphical icons 505 so that each icon is associated with a set of user preferred tools. For example, icons F1-F4 are assigned to segment 1, and each of icons F1-F4 have an associated set of user preferred tools that the processor 210 (or the user) has determined is useful for phase 1 (i.e., segment 1).

In at least one embodiment, hovering a mouse (i.e., a computer mouse) arrow over an icon 505 will display a set (e.g., a sequence) of user preferred tools associated with that icon. For example, if a user hovers the mouse arrow over F1, the interface may display a window 520 with the sequence "zoom in, rotate 90°, measure volume." If the user clicks on F1, the processor 210 will execute the functions of 'zoom in', 'rotate 90°', and 'measure volume' on image A. According to an example embodiment, each of these functions may occur on the UI 500 in sequence.

According to at least another embodiment, the UI 500 is configured to update the user preferred tools associated with each icon 505 as the processor 210 collects and filters additional data about user interaction with each segment. In this case, the UI 500 may include an add/remove icon 515 which, if selected, opens a checkbox 517. The processor 210 may be configured to populate the checkbox with options for additional tools based on previously recorded context information and user habit information. For example, the processor 210 may determine that the tool 'measure diameter' should be offered for icon F1 based on previous user interaction within segment 1 for a different case. From the checkbox 517, the user decides which tools to assign to each icon.

Alternatively or in addition, the processor may automatically (i.e., without user selection from the checkbox 517) add and/or remove tools to/from F1 based on previously recorded context information and user habit information. For example, after overseeing several similar cases, the processor may determine that a fourth tool, e.g., measure diameter, should be added to icon F1. Alternatively, the processor 210 may determine that one of the tools, e.g., 'zoom in', should be removed from F1.

As is evident from the above description of FIG. 5, a user's diagnostic examination of an image during a particular phase may become increasingly automated as the processor 210 collects more context information and more user habit information for that phase.

Figure 6A:
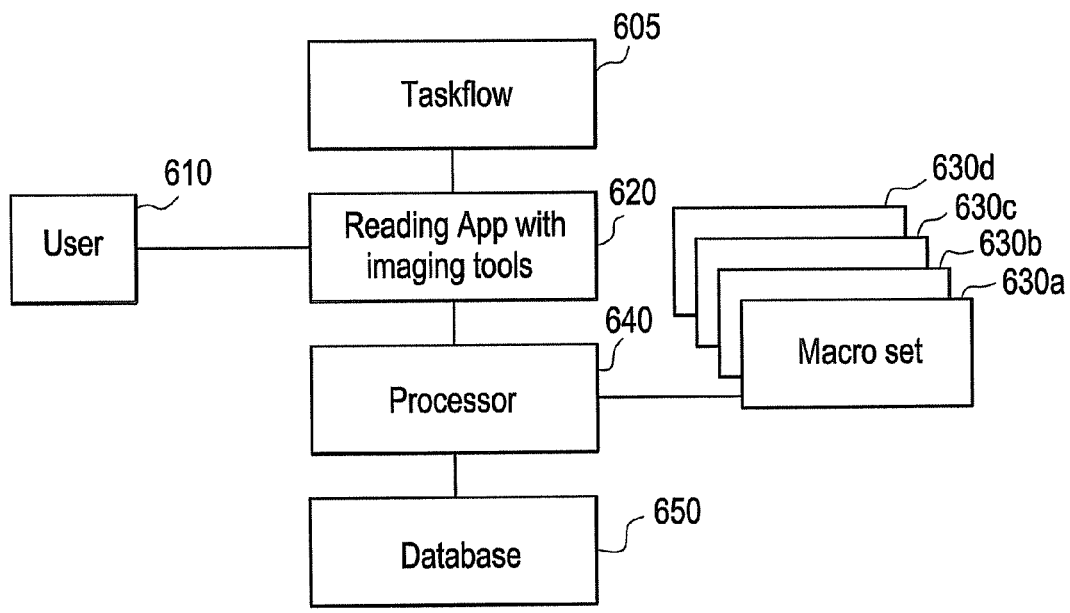
FIGS. 6A-6C are diagrams that illustrate various scenarios of a medical workflow according to at least one example embodiment.
Figure 6B:
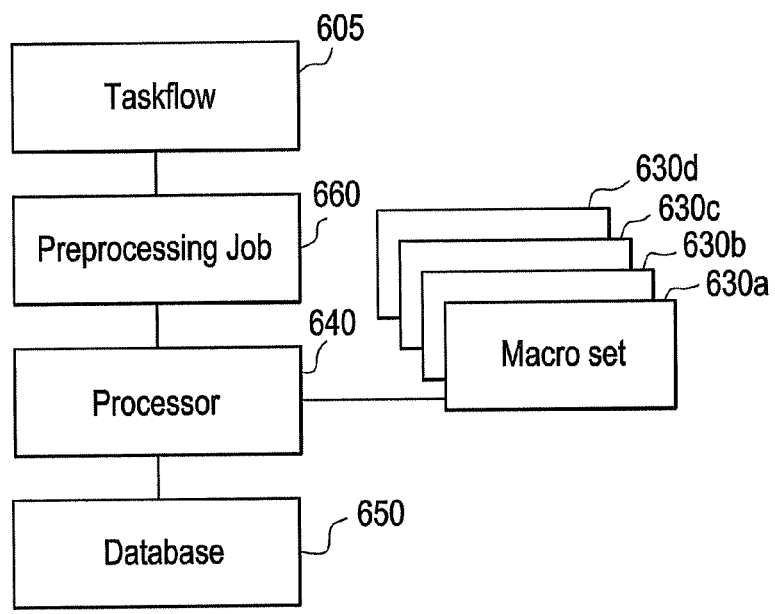
Figure 6C:
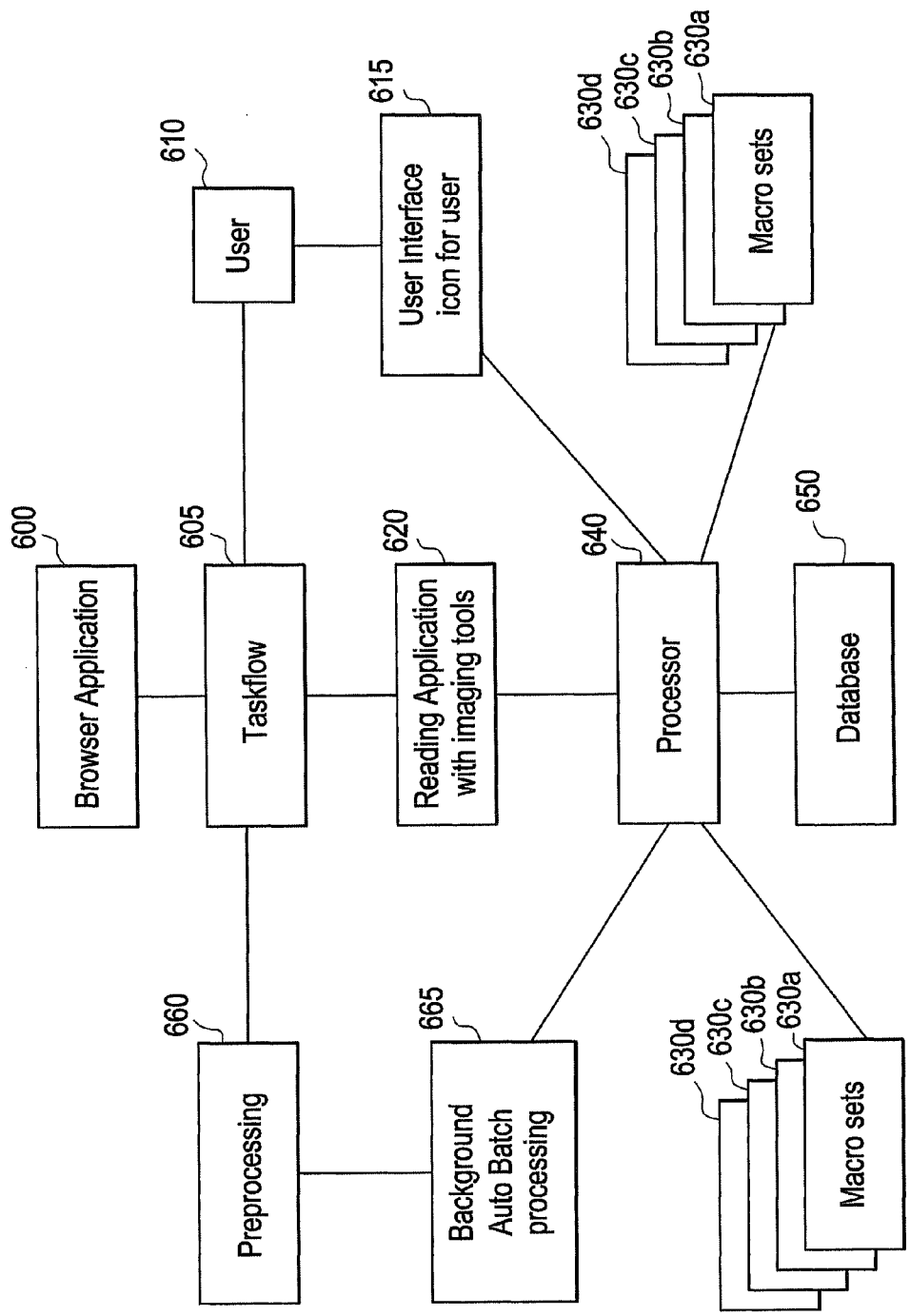

FIGS. 6A-6C are diagrams that illustrate various scenarios of a medical workflow according to at least one example embodiment. For example, a user might want to personalize macro recording during reading a case (i.e., FIG. 6A), macro recording during preprocessing (i.e., FIG. 6B), and/or select personalized macros for the user-selected workflow (i.e., FIG. 6C).

FIG. 6A illustrates that processor 640 scans and records user interaction during a user's 610 reading 620 of a selected case during a particular task flow 605. The processor 640 may correspond to processor 210 in FIG. 2. In FIG. 6A, the processor 640 generates macro sets 630a-630b based on recorded context information (e.g., the context of task flow 605) and user habit information (e.g., which imaging tools the user selects) collected during this scan. Although four macro sets are shown, it should be understood that example embodiments are not limited thereto. The processor 640 may generate any number of macros based on the recorded context information and user habit information. Each macro set 630a-630d may contain one or more macros. The processor 640 may store the generated macro sets 630a-630d in a database 650.

The database 650 may be a cloud based database that contains user specific settings, commonly used phases and sub-phases, and macros programs. The content of database 650 is not medical data, but software programs. Thus, legal restrictions associated with medical data, which can hamper the export of data from the hospital to a public cloud environment, do not apply.

According to an example embodiment, user 610 may query the database 650 to recall a stored macro set to view available add-ons to automate their workflow in a personalized way. The user 610 may assign query results (i.e., the recalled macro set) to 'programmable' icons on the UI. The assigned icon offers the execution of the recalled macro set when the user executes a desired phase.

FIG. 6B illustrates that processor 640 scans the preprocessing activities (i.e., the activity that occurs before the imaging application is opened; this activity may include, for example, calculating 3D volume data from 2D input data, or label the spine; this information is then available to the user as soon as the application is opened) and generates the macro sets 630a-630d based on preprocessing activity, and stores the generated macro sets into the database 650. Afterwards, either upon user request or automatically, the user may view these activities in terms of macro sets 630a-630d and alter or extend a macro set via, for example, a text window on the user interface.

FIG. 6C illustrates a use case for an imaging application Browser_App 600. Before the task flow 605 begins, and during user interaction, the processor 640 makes the functionality of macro sets 630a-630d available to pre-processing and to the user 610 that is available for the phases that are 'due' in the task flow 605. The user 610 has personalized functionality available via dedicated UI icons 615, for example.

The Browser_App 600 contains multiple data sets in a worklist view. For each of these data sets, the user may adjust the personalization. For example, the user may adjust which macros are executed now or next time (preprocessing) and/or which macros are shown (reading application). Such personalization settings may be bound to the type of image data (e.g. CT scans or MR scans) and/or bound to the mapped work flow (e.g. routine reading, or MR Onco advanced reading). The user may query the database 650 for stored macro sets. The processor 640 matches the stored macros back to the targeted preprocessing jobs (e.g., via background auto batch processing 665) and applications, using the job/application name, the names of the UI controls and plug-ins, and/or the element names that denoted the start of a phase. This creates a high level of reliability for the user because the macro sets work not only in the same application but also in a 'foreign' target job or application. Also, the user 610 may deselect some application tools if some of the query results are not applicable. As the next step, the user 610 selects a data set in the worklist and starts reading the data set in the reading application 620.

Overall, example embodiments provide at least the following core capabilities:

- macros are auto-collected and offered to the user for later use;
- macros are mapped to a tree of desired (or alternatively, predefined) phases into which the medical workflow or the interaction has been cut (like an activity diagram) in order to support each phase with adequate automation upon user request;
- macros may be copied between imaging applications and workflows, and if desired, may be re-compiled for a different imaging application;
- macros that are copied use a target tree with the application phases as context to match with the phase the macros have been created in;
- the system offers a user to edit (e.g. add and/or remove) tools from a macro, and/or store or ignore new macros;
- auto federation with macros to other applications and workflows is enabled; and
- the UI of the clinical application offers new automation functionality that may be selected by the user during routine or advanced reading, for example (e.g., the graphical icons may change their associated user-preferred tools depending on the current phase so if a the user is in a particular phase, macros for that phase are assigned to the icons; if filming or reporting is open, the functionality is specific to filming or reporting).

Accordingly, a user of a clinical workstation may, while reading an image, run a personal sequence of automated tools with one click, instead of having to select each tool from the multi-level corner menus. This optimizes and accelerates the work pattern of the user. The same underlying mechanisms allow the clinical workstation to perform conditional workflow mapping for the user, and customize preprocessing automatically. The user may also copy macros into his environment (from, e.g., database 650).

Further, example embodiments allow coupling knowledge databases with application functionality upfront (before the task flow starts) in order to map the best-fit workflow, adjust the applications in the workflow (add the right ad hoc task, for example), and load a focused selection of tools into the applications.

Other advantages include easy re-play for clinical demos, and support for unattended Application Trainings on live-systems. An important advantage for the user is more perceived performance for UI handling and the time saved from a more focused preprocessing.

One embodiment of the present application includes a computer readable medium. The computer readable medium includes code segments that, when executed by a processor, cause the processor to perform the above described steps with reference to FIGS. 4A and 4B.

While example embodiments have been particularly shown and described, it will be understood by one of ordinary skill in the art that variations in form and detail may be made therein without departing from the spirit and scope of the claims. The invention being thus described, it will be obvious that the same may be varied in many ways. Such variations are not to be regarded as a departure from the invention, and all such modifications are intended to be included within the scope of the invention.

We claim:

1. A clinical workstation, comprising:
   a processor configured to,
      record context information and user habit information based on user interaction with a computer-based application during a plurality of phases of a medical workflow, wherein the workflow is divided into phases according to an existing structure of a medical domain, the user habit information being recorded by,
         assigning first identifiers to each of the plurality phases,
         assigning second identifiers to control elements of the computer-based application,
         using the first identifiers and the second identifiers to match the control elements with the corresponding phases,
         detecting the user interaction with the control elements, and
         recording events and user interactions for each phase as the user habit information,
      and
      generate a plurality of macro sets based on the recorded context information and the recorded user habit information, each macro set being associated with at least one user preferred application tool and being bound to one of the plurality of phases.

2. The clinical workstation of claim 1, further comprising:
a display configured to display a user interface of the computer-based application, wherein the processor is further configured to,
assign each macro set to graphical icons of the user interface, the graphical icons automating a usage of the at least one user preferred application tool.

3. The clinical workstation of claim 1, wherein the processor is configured to,
detect a boundary for each of the plurality of phases by evaluating elements of the computer-based application,
mark the boundary for each of the plurality of phases, and
record the context information and the user habit information based on the marked boundaries.

4. The clinical workstation of claim 2, wherein the processor is configured to store the plurality of macro sets in an external database.

5. The clinical workstation of claim 2, wherein, upon selection of one of the graphical icons, the processor is configured execute the macro set assigned to the selected graphical icon such that the at least one preferred application tool is executed on the user interface.

6. The clinical workstation of claim 4, wherein the processor is further configured to,
query the external database to recall a stored macro set,
assign the recalled macro set to the one or more graphical icons to generate updated graphical icons, and
display the updated graphical icons on the interface.

7. The clinical workstation of claim 6, wherein the processor is configured to query the external database in response to a user request.

8. The clinical workstation of claim 6, wherein the processor is configured to automatically query the external database.

9. The clinical workstation of claim 6, wherein the processor is configured to execute the recalled macro set associated with the updated graphical icons such that functions of the user preferred application tools are executed on the interface.

10. The clinical workstation of claim 6, wherein the processor is configured to allow the user to assign the recalled macro set to the graphical icons.

11. The clinical workstation of claim 6, wherein the processor is configured to automatically assign the recalled macro set to the graphical icons based on previously recorded context information and user habit information stored in the database.

12. A method, comprising:
recording context information and user habit information based on user interaction with a computer-based application during a plurality of phases of a medical workflow, wherein the workflow is divided into phases according to an existing structure of a medical domain, the user habit information being recorded by,
assigning first identifiers to each of the plurality of phases,
assigning second identifiers to control elements of the computer-based application,
using the first identifiers and the second identifiers to match the control elements with the corresponding phases,
detecting the user interaction with the control elements, and
recording events and user interactions for each phase as the user habit information; and
generating a plurality of macro sets based on the recorded context information and the recorded user habit information, each macro set being associated with at least one user preferred application tool and being bound to one of the plurality of phases.

13. The method of claim 12, further comprising:
assigning each macro set to graphical icons on a user interface of the computer-based application, the graphical icons automating a usage of the at least one user preferred application tool; and
displaying the user interface on a display.

14. The method of claim 12, further comprising:
detecting a boundary for each of the plurality of phases by evaluating elements of the computer-based application;
marking the boundary for each of the plurality of phases, wherein the recording the context information and the user habit information occurs based on the marked boundaries.

15. The method of claim 13, further comprising:
storing the plurality of macro sets in an external database.

16. The method of claim 13, further comprising:
executing, upon selection of one of the graphical icons, the macro set assigned to the selected graphical icon such that the at least one preferred application tool is executed on the interface.

17. The method of claim 15, further comprising:
querying the external database to recall a stored macro set,
assigning the recalled macro set to the one or more graphical icons to generate updated graphical icons, and
displaying the updated graphical icons on the user interface.

18. The method of claim 17, wherein the querying the external database occurs in response to a user request.

19. The method of claim 17, wherein the querying occurs automatically.

20. The method of claim 17, further comprising:
executing the recalled macro set associated with the updated graphical icons such that functions of the user preferred application tools are executed on the interface.

21. The method of claim 17, further comprising:
allowing the user to assign the recalled macro set to the graphical icons.

22. The method of claim 17, further comprising:
automatically assigning the recalled macro set to the graphical icons based on previously recorded context information and user habit information stored in the database.

23. The method of claim 12, further comprising:
dividing the medical workflow into the plurality of phases.

24. A non-transitory computer readable medium including instructions for, if executed by a computer processor, causing the computer processor to implement the method of claim 12.

25. A non-transitory computer readable medium including instructions for, if executed by a computer processor, causing the computer processor to implement the method of claim 13.

26. A clinical workstation, comprising:
a processor configured to generate a user interface for a computer-based application, the user interface including,
at least one segment configured to display an image related to a medical workflow, wherein the workflow is divided into phases according to an existing structure of a medical domain, and
at least one first icon configured to automate a usage of at least one user preferred application tool of the computer-based application, the at least one first icon being assigned to the at least one segment and associated with one or more macros, the one or more macros being based on context information and user habit information recorded during user interaction with the at least one segment, wherein the processing unit is configured to record the user habit information by,
  assigning first identifiers to each of the plurality phases,
  assigning second identifiers to control elements of the computer-based application,
  using the first identifiers and the second identifiers to match the control elements with the corresponding phases,
  detecting the user interaction with the control elements, and
  recording events and user interactions for each phase as the user habit information.

27. The user interface of claim 26, further comprising:
a second icon configured to control whether a processor records the user context information and user habit information; and
a third icon configured to allow the user to at least one of add and remove user preferred application tools to or from the at least one icon.

* * * * *